US010332633B2

(12) United States Patent
Duke et al.

(10) Patent No.: US 10,332,633 B2
(45) Date of Patent: Jun. 25, 2019

(54) CONTROL-TO-RANGE AGGRESSIVENESS

(71) Applicant: Roche Diabetes Care, Inc., Indianapolis, IN (US)

(72) Inventors: David L. Duke, Fishers, IN (US); Alan Greenburg, Indianapolis, IN (US); Christian Ringemann, Mannheim (DE); Chinmay Uday Manohar, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 292 days.

(21) Appl. No.: 15/170,450

(22) Filed: Jun. 1, 2016

(65) Prior Publication Data

US 2017/0348483 A1 Dec. 7, 2017

(51) Int. Cl.
*A61M 5/142* (2006.01)
*A61M 5/172* (2006.01)
(Continued)

(52) U.S. Cl.
CPC ............ *G16H 50/20* (2018.01); *A61M 5/142* (2013.01); *A61M 5/1723* (2013.01);
(Continued)

(58) Field of Classification Search
CPC ....... G16H 50/20; G16H 40/63; A61M 5/142; A61M 5/1723; G06F 19/00
(Continued)

(56) References Cited

U.S. PATENT DOCUMENTS 6,572,545 B2 6/2003 Knobbe et al.
6,575,905 B2 6/2003 Knobbe et al.
(Continued)

FOREIGN PATENT DOCUMENTS

EP 2762073 A1 8/2014
WO 2002/24065 A1 3/2002
(Continued)

OTHER PUBLICATIONS

International Search Report pertaining to Appln. No. PCT/US2017/019025, filed Feb. 23, 2017, 5 pages.
(Continued)

*Primary Examiner* — Phillip A Gray
(74) *Attorney, Agent, or Firm* — Dinsmore & Shohl LLP

(57) ABSTRACT

A method and system of determining a basal rate adjustment of insulin in a continuous glucose monitoring system of a person with diabetes is provided. The method includes receiving, by at least one computing device, a signal representative of at least one glucose measurement; detecting, by the at least one computing device, a glucose state of the person based on the signal, the detected glucose state including a glucose level of the person and a rate of change of the glucose level; determining, by the at least one computing device, a current risk metric, the current risk metric indicating a risk of at least one of a hypoglycemic condition and a hyperglycemic condition of the person; and calculating, by the at least one computing device, an adjustment to a basal rate of a therapy delivery device based on the current risk metric and a control-to-range algorithm comprising at least one aggressiveness parameter.

15 Claims, 10 Drawing Sheets

(51) Int. Cl.
*G16H 50/20* (2018.01)
*G06F 19/00* (2018.01)
*G16H 40/63* (2018.01)

(52) U.S. Cl.
CPC ......... *G06F 19/3468* (2013.01); *G16H 40/63* (2018.01); *A61M 2005/14208* (2013.01); *A61M 2205/50* (2013.01); *A61M 2205/502* (2013.01); *A61M 2205/52* (2013.01); *A61M 2205/8212* (2013.01); *A61M 2230/201* (2013.01)

(58) Field of Classification Search
USPC .................................................. 604/500–504
See application file for complete search history.

(56) References Cited

U.S. PATENT DOCUMENTS

| | | |
|---|---|---|
| 7,291,107 B2 | 11/2007 | Hellwig et al. |
| 7,395,158 B2 | 7/2008 | Monfre et al. |
| 7,785,313 B2 | 8/2010 | Mastrototaro |
| 8,579,854 B2 | 11/2013 | Budiman et al. |
| 8,579,879 B2 | 11/2013 | Palerm et al. |
| 8,684,922 B2 | 4/2014 | Tran |
| 8,734,422 B2 | 5/2014 | Hayter |
| 8,843,321 B2 | 9/2014 | Duke et al. |
| 8,977,504 B2 | 3/2015 | Hovorka |
| 9,247,901 B2 | 2/2016 | Kamath et al. |
| 2002/0106709 A1 | 8/2002 | Potts et al. |
| 2004/0167464 A1 | 8/2004 | Ireland et al. |
| 2006/0047192 A1 | 3/2006 | Hellwig et al. |
| 2009/0105572 A1 | 4/2009 | Malecha |
| 2010/0262434 A1 | 10/2010 | Shaya |
| 2011/0071464 A1 | 3/2011 | Palerm |
| 2011/0184267 A1 | 7/2011 | Duke et al. |
| 2011/0257627 A1 | 10/2011 | Hovorka |
| 2011/0313674 A1 | 12/2011 | Duke et al. |
| 2012/0165638 A1 | 6/2012 | Duke et al. |
| 2012/0166126 A1 | 6/2012 | Engelhardt et al. |
| 2014/0005505 A1 | 1/2014 | Peyser et al. |
| 2014/0066884 A1 | 3/2014 | Keenan et al. |
| 2014/0066887 A1 | 3/2014 | Mastrototaro et al. |
| 2014/0081103 A1 | 3/2014 | Schaible |
| 2014/0083867 A1 | 3/2014 | Schaible |
| 2014/0088392 A1 | 3/2014 | Bernstein et al. |
| 2014/0100435 A1 | 4/2014 | Duke et al. |
| 2014/0118138 A1 | 5/2014 | Cobelli et al. |
| 2014/0187887 A1 | 7/2014 | Dunn et al. |
| 2014/0188400 A1 | 7/2014 | Dunn et al. |
| 2014/0221966 A1 | 8/2014 | Buckingham et al. |
| 2014/0235981 A1 | 8/2014 | Hayter |
| 2015/0273147 A1* | 10/2015 | Duke ............... A61M 5/1723 604/504 |

FOREIGN PATENT DOCUMENTS

| | | |
|---|---|---|
| WO | 0224065 A1 | 3/2002 |
| WO | 2013/032965 A1 | 3/2013 |
| WO | 2014/106263 A2 | 7/2014 |
| WO | 2015/183689 A1 | 3/2015 |
| WO | 2015073211 A1 | 5/2015 |

OTHER PUBLICATIONS

Written Opinion pertaining to Appln. No. PCT/US2017/019025, filed Feb. 23, 2017, 8 pages.
International Search Report pertaining to Appln. No. PCT/US2017/019013, filed Feb. 23, 2017, 5 pages.
Written Opinion pertaining to Appln. No. PCT/US2017/019013, filed Feb. 23, 2017, 8 pages.
Bruno Sinopoli, et al., Kalman Filtering With Intermittent Observations, DARPA under grant F33615-01-C-1895, 28 pages.
David Di Ruscio, Closed and Open Loop Subspace System Identification of the Kalman Filter, 2009 Norwegian Society of Automatic Control, vol. 30, No. 2 , 2009, pp. 71-86, ISSN 1890-1328, Norway.
J. Zico Kolter, et al., A Probabilistic Approach to Mixed Open-loop and Closed-loop Control, with Application to Extreme Autonomous Driving, Computer Science Department, Stanford University, California (kolter@cs.stanford.edu), 7 pages, USA.
Chiara Toffanin, et al., Artificial Pancreas: Model Predictive Control Design from Clinical Experience, Journal of Diabetes Science and Technology, pp. 1470-1483, vol. 7, Issue 6, Nov. 2013, USA.
Signe Schmidt, et al., Model-Based Closed-Loop Glucose Control in Type 1 Diabetes: The DiaCon Experience, Journal of Diabetes Science and Technology, pp. 1255-1264, vol. 7, Issue 5, Sep. 2013, USA.
Schwartz et al., "Use of Automated Bolus Calculators for Diabetes Management," Diabetes Management, Touch Medical Media 2013, 92-95.
International Search Report and Written Opinion completed Jun. 10, 2016 pertaining to PCT/US2016/025502 filed Apr. 1, 2016.
Kovatchev et al., "Symmetrization of the Blood Glucose Measurement Scale and Its Applications,", Diabetes Care, 1997, vol. 20, No. 11, 1655-1658.
Lucero et al., "On the Registration of Time and the Patterning of Speech Movements," Journal of Speech, Language, and Hearing Research 40: 1111-1117.
Ward, "Hierarchical Grouping to Optimize an Objective Function," Journal of the American Statistical Association, 1963, vol. 58, Issue 301, 236-244.
Kaufman et al., Finding Groups in Data: An Introduction to Cluster Analysis (1 ed.), New York: John Wiley, ISBN 0-471-87876-6 (BOOK).
Sakoe et al., "Dynamic Programming Algorithm Optimization for Spoken Word Recognition," IEEE Transactions on Acoustics, Speech and Signal Processing 26 (1): 43-49.
Takita et al., "Cluster Analysis of Self-Monitoring Blood Glucose Assessments in Clinical Islet Cell Transplantation for Type 1 Diabetes," Diabetes Care, vol. 34, 2011, 1799-1803.
International Search Report pertaining to Appln. No. PCT/US2017/019030, filed Feb. 23, 2017, 5 pages.
Written Opinion pertaining to Appln. No. PCT/US2017/019030, filed Feb. 23, 2017, 9 pages.
U.S. Non-Final Office Action dated May 31, 2018 pertaining to U.S. Appl. No. 15/170,468, 12 pages.
International Search Report dated Aug. 21, 2017, pertaining to PCT/US2017/029072, filed Apr. 24, 2017, 6 pages.
Written Opinion dated Aug. 21, 2017, pertaining to PCT/US2017/029072, filed Apr. 24, 2017, 14 pages.
Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
U.S. Non-Final Office Action dated Sep. 5, 2017 pertaining to U.S. Appl. No. 14/677,148, 13 Pages.
International Search Report pertaining to PCT application No. PCT/US2017/031661, filed May 9, 2017, 6 pages.
Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using continuous Glucose Monitoring and Insulin Pump Data, Journal of Diabetes Science and Technology, vol. 4, No. 5, Sep. 1, 2010, pp. 1146-1155, USA.
Pickup et al. (Continuous Subcutaneous Insulin Infusion at 25 Years, Diabetes Care 2002, 25, 593-598).

* cited by examiner

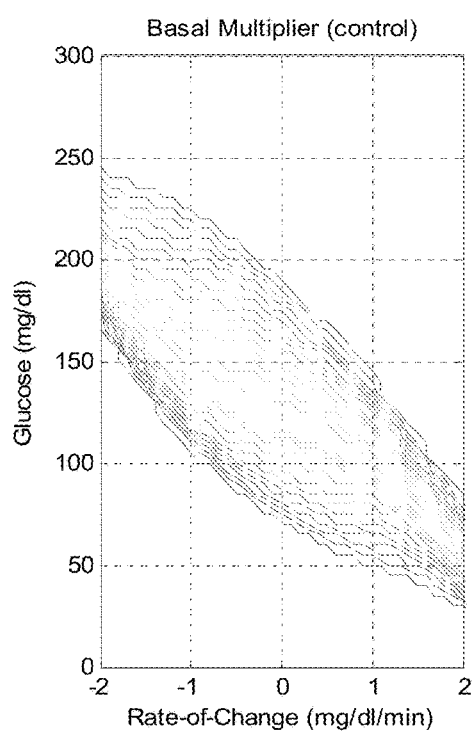
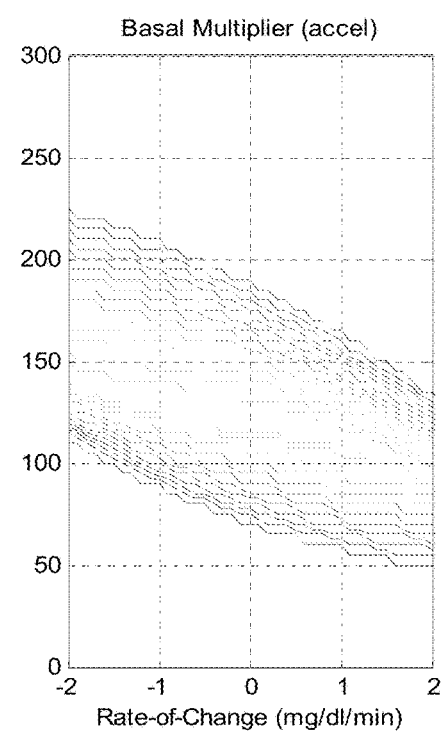
FIG. 6A
FIG. 6B

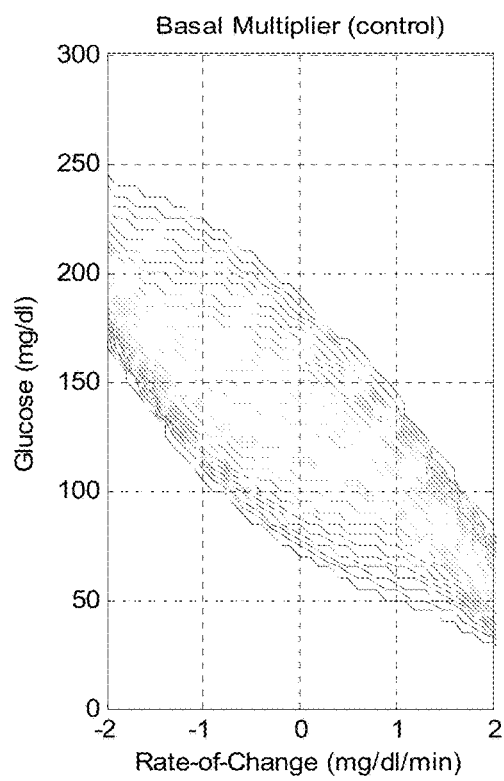
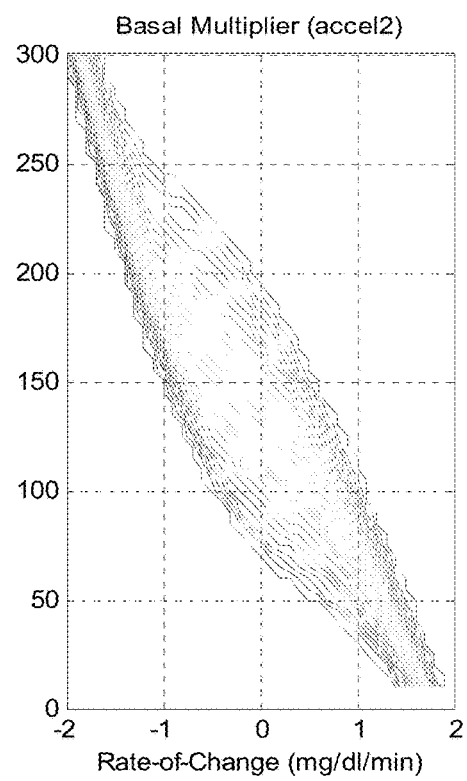
FIG. 7A
FIG. 7B

CONTROL-TO-RANGE AGGRESSIVENESS

TECHNICAL FIELD

The present invention generally relates to processing glucose data measured from a person having diabetes and, in particular, for controlling an adjustment to a basal rate of a therapy delivery device based on the current risk metric and a control-to-range algorithm comprising at least one aggressiveness parameter.

BACKGROUND

As background, people suffer from either Type I or Type II diabetes in which the sugar level in the blood is not properly regulated by the body. Many of these people may use a continuous glucose monitoring (CGM) to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every one minute, and transmit the results of the glucose measurement result to an insulin pump, blood glucose meter, smart phone or other electronic monitor.

In some cases, the measured glucose results (from the glucose sensor) may not accurately represent the glucose concentration. The glucose sensor may malfunction from time to time, such that the measured glucose results (from the glucose sensor) may be substantially different than the actual glucose level of the person. The glucose sensor may malfunction in this manner due to, for example, failure of the sensor electronics or battery or due to sensor "dropout." Sensor dropout may occur due to physiological problems with the glucose sensor's attachment to the person, such as movement of the sensor relative to the person. Sensor dropout may cause the measured glucose results "drop" to near zero, although the actual glucose level of the person may be much higher. Additionally, the calibration of the glucose sensor may drift resulting in a bias toward greater than the true current blood glucose level or less than the true current blood glucose level. The glucose sensor may also experience an error which causes the CGM to no longer response to changes in the true blood glucose level and remain at an incorrect artificially high or artificially low blood glucose reading. Finally, a glucose sensor may be in the first day of use and have error in blood glucose measurement until stabilization.

As a result, embodiments of the present disclosure may process the measured glucose results from the person such that the actual glucose level of the person may be estimated, even in the presence of sensor noise and/or sensor malfunction. In addition, the future glucose level of the person may be predicted, based on the estimated glucose level.

As a result, embodiments of the present disclosure may implement an aggressiveness parameter in adjusting basal insulin rates to account for glucose sensor error.

SUMMARY

In one embodiment, a method of determining a basal rate adjustment of insulin in a continuous glucose monitoring system of a person with diabetes is provided. The method includes receiving, by at least one computing device, a signal representative of at least one glucose measurement. Further, the method includes detecting, by the at least one computing device, a glucose state of the person based on the signal, the detected glucose state including a glucose level of the person and a rate of change of the glucose level. Additionally, the method includes determining, by the at least one computing device, a current risk metric, the current risk metric indicating a risk of at least one of a hypoglycemic condition and a hyperglycemic condition of the person. Finally, the method includes calculating, by the at least one computing device, an adjustment to a basal rate of a therapy delivery device based on the current risk metric and a control-to-range algorithm comprising at least one aggressiveness parameter.

In another embodiment, a blood glucose management device configured to determine a basal rate adjustment in a continuous glucose monitoring system of a person with diabetes is provided. The device includes a non-transitory computer-readable medium storing executable instructions and at least one processing device configured to execute the executable instructions such that, when executed by the at least one processing device, the executable instructions cause the at least one processing device to receive a signal representative of at least one glucose measurement. Additionally, the executable instructions cause the at least one processing device to detect a glucose state of the person based on the signal, the detected glucose state including a glucose level of the person and a rate of change of the glucose level. Further, the executable instructions cause the at least one processing device to determine a current risk metric, the current risk metric indicating a risk of at least one of a hypoglycemic condition and a hyperglycemic condition of a person. Finally, the executable instructions cause the at least one processing device to calculate an adjustment to a basal rate of a therapy delivery based on the current risk metric and a control-to-range algorithm comprising at least one aggressiveness parameter.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

FIGS. 6A and 6B illustrate typical basal multipliers and basal multipliers with implementation of an increased maximum allowed acceleration aggressiveness parameter respectively according to one or more embodiments shown and described herein;

FIGS. 7A and 7B illustrate typical basal multipliers and basal multipliers with implementation of a decreased maximum allowed aggressiveness parameter respectively according to one or more embodiments shown and described herein;

DETAILED DESCRIPTION

The embodiments described herein generally relate to methods and systems for determining a basal rate adjustment of insulin in a continuous glucose monitoring system of a person with diabetes and, in particular, for implementing at least one aggressiveness parameter in determining adjustments to basal rate. For the purposes of defining the present disclosure, the "measured glucose results" are the glucose levels of the person as measured by the glucose sensor; the "actual glucose level" or "true glucose measurement" is the actual glucose level of the person.

Figure 1:
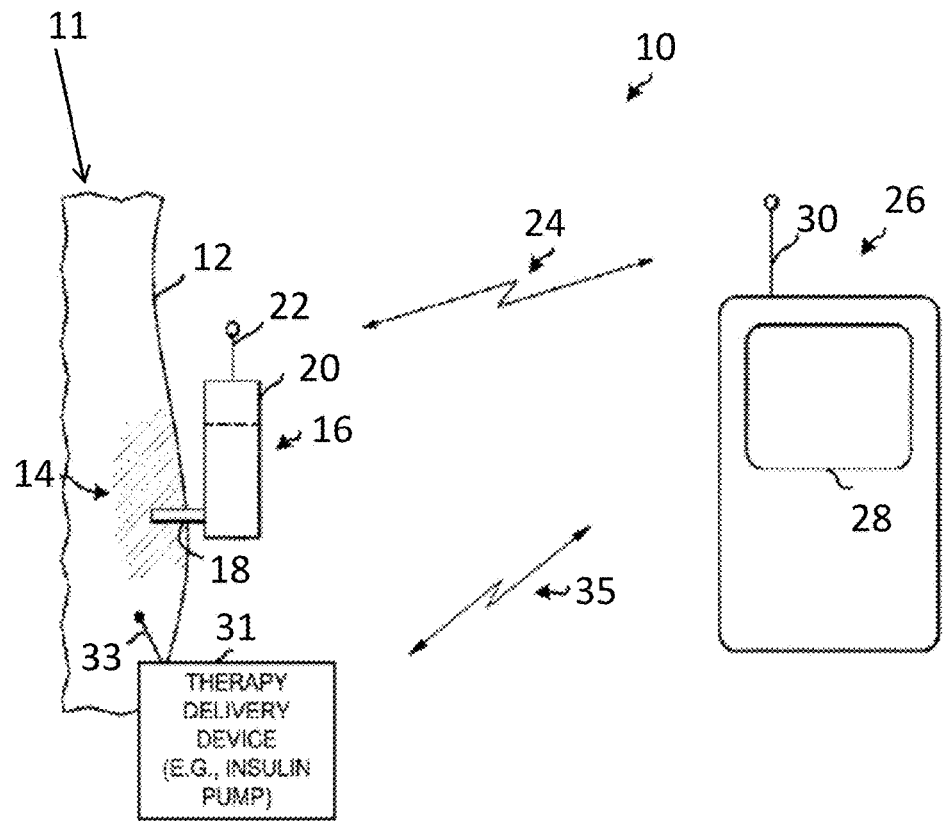
FIG. 1 illustrates a continuous glucose monitoring (CGM) system according to one or more embodiments shown and described herein.

Referring to FIG. 1, an exemplary continuous glucose monitoring (CGM) system 10 is illustrated for monitoring the glucose level of a person with diabetes (PWD) 11. In particular, CGM system 10 is operative to collect a measured glucose value at a predetermined, adjustable interval, such as every one minute, five minutes, or at other suitable intervals. CGM system 10 illustratively includes a glucose sensor 16 having a needle or probe 18 that is inserted under the skin 12 of the person. The end of the needle 18 is positioned in interstitial fluid 14, such as blood or another bodily fluid, such that measurements taken by glucose sensor 16 are based on the level of glucose in interstitial fluid 14. Glucose sensor 16 is positioned adjacent the abdomen of the person or at another suitable location. Furthermore, the glucose sensor 16 may be periodically calibrated in order to improve its accuracy. This periodic calibration may help correct for sensor drift due to sensor degradation and changes in the physiological condition of the sensor insertion site. Glucose sensor 16 may comprise other components as well, including but not limited to a wireless transmitter 20 and an antenna 22. Glucose sensor 16 may alternatively use other suitable devices for taking measurements, such as, for example, a non-invasive device (e.g., infrared light sensor). Upon taking a measurement, glucose sensor 16 transmits the measured glucose value via a communication link 24 to a computing device 26, illustratively a blood glucose (bG) management device 26. The bG management device 26 may also be configured to store in memory 39 a plurality of measured glucose results received from the glucose sensor 16 over a period of time.

CGM system 10 further includes a therapy delivery device 31, illustratively an insulin infusion pump 31, for delivering therapy (e.g., insulin) to the person. Insulin pump 31 is in communication with management device 26 via a communication link 35, and management device 26 is able to communicate bolus and basal rate information to insulin pump 31. Insulin pump 31 includes a catheter 33 having a needle that is inserted through the skin 12 of the person 11 for injecting the insulin. Insulin pump 31 is illustratively positioned adjacent the abdomen of the person or at another suitable location. Similar to glucose sensor 16, infusion pump 31 also includes a wireless transmitter and an antenna for communication with management device 26. Insulin pump 31 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 26. Similarly, the basal rate of the basal insulin is set based on user input or in response to a command from management device 26. Infusion pump 31 may include a display for displaying pump data and a user interface providing user controls. In an alternative embodiment, insulin pump 31 and glucose sensor 16 may be provided as a single device worn by the patient, and at least a portion of the logic provided by processor or microcontroller may reside on this single device. Bolus insulin may also be injected by other means, such as manually by the user via a needle.

In one embodiment, such a CGM system 10 is referred to as an artificial pancreas system that provides closed loop or semi-closed loop therapy to the patient to approach or mimic the natural functions of a healthy pancreas. In such a system, insulin doses are calculated based on the CGM readings and are automatically delivered to the patient based on the CGM reading. For example, if the CGM indicates that the user has a high blood glucose level or hyperglycemia, the system can calculate an insulin dose necessary to reduce the user's blood glucose level below a threshold level or to a target level and automatically deliver the dose. Alternatively, the system can automatically suggest a change in therapy such as an increased insulin basal rate or delivery of a bolus, but can require the user to accept the suggested change prior to delivery. If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, suggest that the user, e.g., ingest carbohydrates and/or automatically take other actions and/or make other suggestions as may be appropriate to address the hypoglycemic condition, singly or in any desired combination or sequence. In some embodiments, multiple medicaments can be employed in such a system such as a first medicament, e.g., insulin, that lowers blood glucose levels and a second medicament, e.g., glucagon, which raises blood glucose levels.

Communication links 24, 35 are illustratively wireless, such as a radio frequency ("RF") or other suitable wireless frequency, in which data and controls are transmitted via electromagnetic waves between sensor 16, therapy delivery device 31, and management device 26. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 24, 35 may facilitate communication between multiple devices, such as between glucose sensor 16, computing device 26, insulin pump 31, and other suitable devices or systems. Wired links may alternatively be provided between devices of system 10, such as, for example, a wired Ethernet link. Other suitable public or proprietary wired or wireless links may be used.

Figure 2:
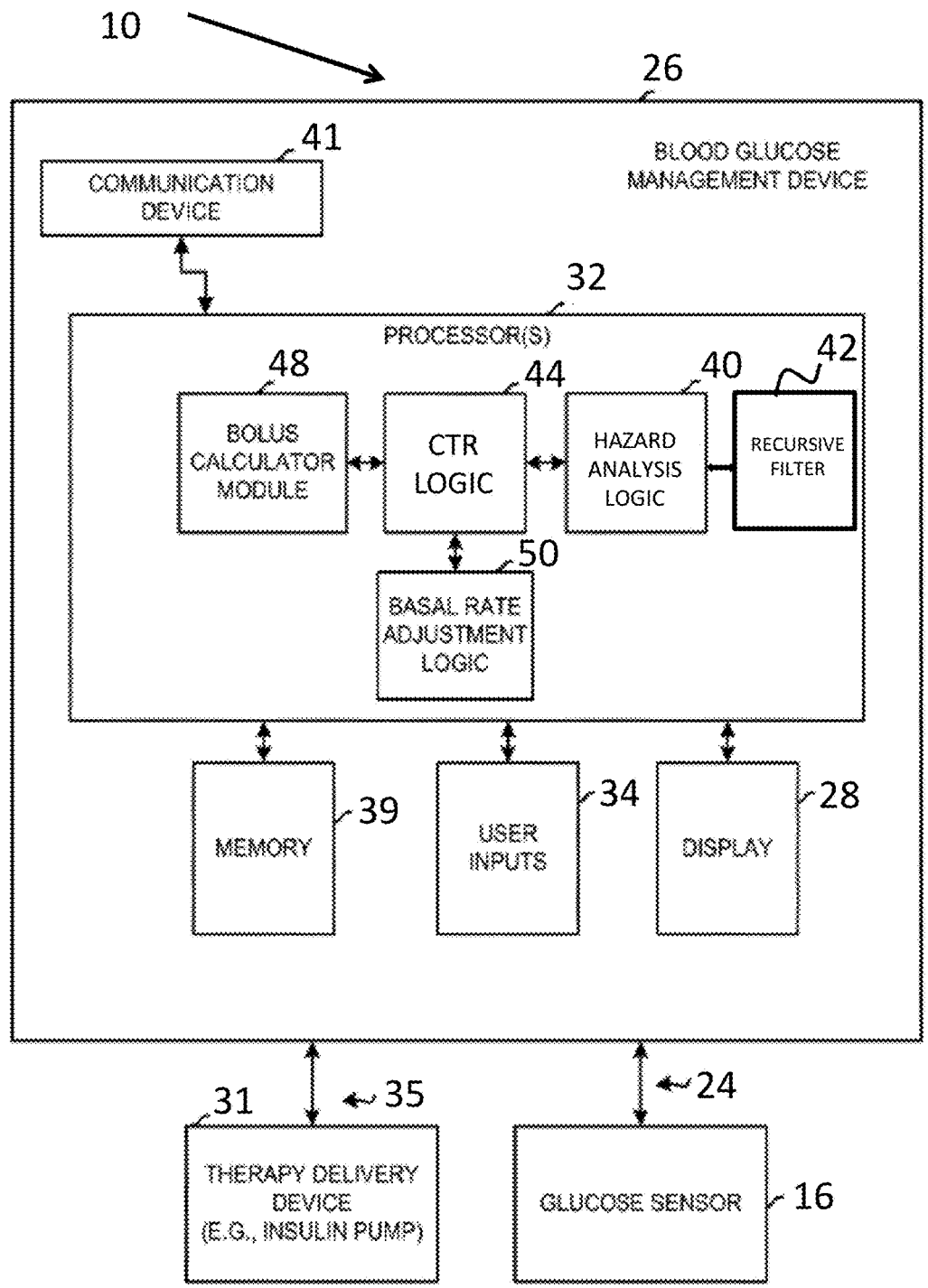
FIG. 2 illustrates an exemplary blood glucose management device, therapy delivery device, and glucose sensor of the CGM system of FIG. 2, the blood glucose management device including a bolus calculator module, control-to-range logic, and basal rate adjustment logic.

FIG. 2 illustrates an exemplary management device 26 of the CGM system 10 of FIG. 2. Management device 26 includes at least one microprocessor or microcontroller 32 that executes software and/or firmware code stored in memory 39 of management device 26. The software/firmware code contains instructions that, when executed by the microcontroller 32 of management device 26, causes management device 26 to perform the functions described herein. Management device 26 may alternatively include one or more application-specific integrated circuits (ASICs), field-programmable gate arrays (FPGAs), digital signal processors (DSPs), hardwired logic, or combinations thereof. While management device 26 is illustratively a glucose monitor 26, other suitable management devices 26 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although management device 26 is illustrated as a single management device 26, multiple computing devices may be used together to perform the functions of management device 26 described herein.

Memory 39 is any suitable computer readable medium that is accessible by microcontroller 32. Memory 39 may be a single storage device or multiple storage devices, may be located internally or externally to management device 26, and may include both volatile and non-volatile media. Further, memory 39 may include one or both of removable and non-removable media. Exemplary memory 39 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by management device 26.

The microcontroller 32 may also include additional programming to allow the microcontroller 32 to learn user preferences and/or user characteristics and/or user history data. This information can be utilized to implement changes in use, suggestions based on detected trends, such as, weight gain or loss. The microcontroller 32 can also include programming that allows the device 26 to generate reports, such as reports based upon user history, compliance, trending, and/or other such data. Additionally insulin infusion pump 31 embodiments of the disclosure may include a "power off" or "suspend" function for suspending one or more functions of the device 26, such as, suspending a delivery protocol, and/or for powering off the device 26 or the delivery mechanism thereof. For some embodiments, two or more microcontrollers 32 may be used for controller functions of insulin infusion pump 31, including a high power controller and a low power controller used to maintain programming and pumping functions in low power mode, in order to save battery life.

Management device 26 further includes a communication device 41 operatively coupled to microcontroller 32. Communication device 41 includes any suitable wireless and/or wired communication module operative to transmit and receive data and controls over communication links 24, 35 between device 26 and glucose sensor 16 and insulin pump 31. In one embodiment, communication device 41 includes an antenna 30 (FIG. 1) for receiving and/or transmitting data wirelessly over communication links 24, 35. Management device 26 stores in memory 39 measured glucose results and other data received from glucose sensor 16 and/or insulin pump 31 via communication device 41.

Management device 26 includes one or more user input device(s) 34 for receiving user input. Input device(s) 34 may include pushbuttons, switches, a mouse pointer, keyboard, touchscreen, or any other suitable input device. Display 28 is operatively coupled to microcontroller 32, and may comprise any suitable display or monitor technology (e.g., liquid crystal display, etc.) configured to display information provided by microcontroller 32 to a user. Microcontroller 32 is configured to transmit to display 28 information related to the detected glucose state of the person, the risk associated with the glucose state, and basal rate and bolus information. The glucose state may include the estimated glucose level and the estimated rate-of-change of the glucose level, as well as an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 to 70 milligrams of glucose per deciliter of blood (mg/dl). Management device 26 may also be configured to tactilely communicate information or warnings to the person, such as for example by vibrating.

In one embodiment, management device 26 is in communication with a remote computing device (not shown), such as at a caregiver's facility or a location accessible by a caregiver, and data (e.g., glucose data or other physiological information) is transferred between them. In this embodiment, management device 26 and the remote device are configured to transfer physiological information through a data connection such as, for example, via the Internet, cellular communications, or the physical transfer of a memory device such as a diskette, USB key, compact disc, or other portable memory device.

Microcontroller 32 also includes control-to-range logic 44. A control-to-range system reduces the likelihood of a hypoglycemic event or a hyperglycemic event by adjusting insulin dosing only if the PWD's 11 glucose level approaches the low or high glucose thresholds.

Microcontroller 32 includes hazard analysis logic 40 that calculates target return paths from a plurality of initial glucose states to a target glucose state based on cumulative hazard values. The target glucose state is illustratively an optimal or ideal glucose state having no associated hazard or risk, such as a glucose level of 112.5 mg/dl and a glucose rate-of-change of zero, although any suitable target glucose state may be identified. Each target return path is comprised of a plurality of intermediate glucose states that are to be encountered during a transition from the initial glucose state to the target glucose state. Cumulative penalty values associated with the target return paths are stored in memory 76 that may be used as a lookup table. Calculation of cumulative penalty values is discussed infra.

In some embodiments, inaccurate glucose measurements may result from malfunction and/or noise associated with glucose sensor 24. As such, hazard analysis logic 40 analyzes the probability of accuracy of the detected glucose state provided with glucose sensor 24. Hazard analysis logic 40 may use any suitable probability analysis tool to determine the probability of accuracy of a measured glucose result, such as a hidden Markov model. Based on the determined probability of accuracy, hazard analysis logic 40 estimates the glucose level and the glucose rate of change of the person using a recursive filter 42. In particular, recursive filter 42, such as a Kalman filter, for example, weights the detected glucose state, including the glucose level and rate of change, with the determined probability of glucose sensor accuracy. Based on the probability of glucose sensor accuracy, recursive filter 42 calculates an uncertainty measure of the estimated glucose state. The uncertainty measure is indicative of the quality of the estimated glucose state. For a series of detected glucose states, the uncertainty for each state may vary.

Microcontroller 32 of FIG. 2 further includes a bolus calculator module 48 that calculates bolus recommendations and a maximum allowed glucose level of a user which may be displayed to a user via display 28. Management device 26 maintains a record in memory 39 of historical data for the user accumulated over time leading up to the current time. The historical data includes blood glucose history, prescription data, prior bolus recommendations, prior administered boluses, prior basal rates, glucose sensitivity factors for the user's sensitivity to insulin and carbohydrates, blood glucose responses to prior boluses and meal events, other user health and medical data, and the time stamp of each event and data recordation. The history data includes patient recorded information such as meal events, amount of carbohydrates consumed, confirmations of bolus deliveries, medications, exercise events, periods of stress, physiological events, manual insulin injections, and other health events, entered via user inputs 34. Bolus calculator module 48 uses the historical data to more accurately and efficiently determine the recommended insulin bolus and/or carbohydrate amount.

The bolus calculator module 48 determines a recommended bolus, such as an insulin correction bolus or a meal bolus, particular to the user based on the current glucose state, the history data, and user input. A suggested meal bolus (e.g., carbohydrate amount) may be in response to a detected or predicted hypoglycemic condition. A suggested correction bolus of insulin may be in response to the detected glucose exceeding the maximum allowable glucose level. The actual amount of carbohydrates consumed and the actual amount of insulin administered may be confirmed by the user as information entered via user inputs 34 and recorded in memory 39 with other history data. The recommended bolus may be displayed on display 28.

Figure 3:
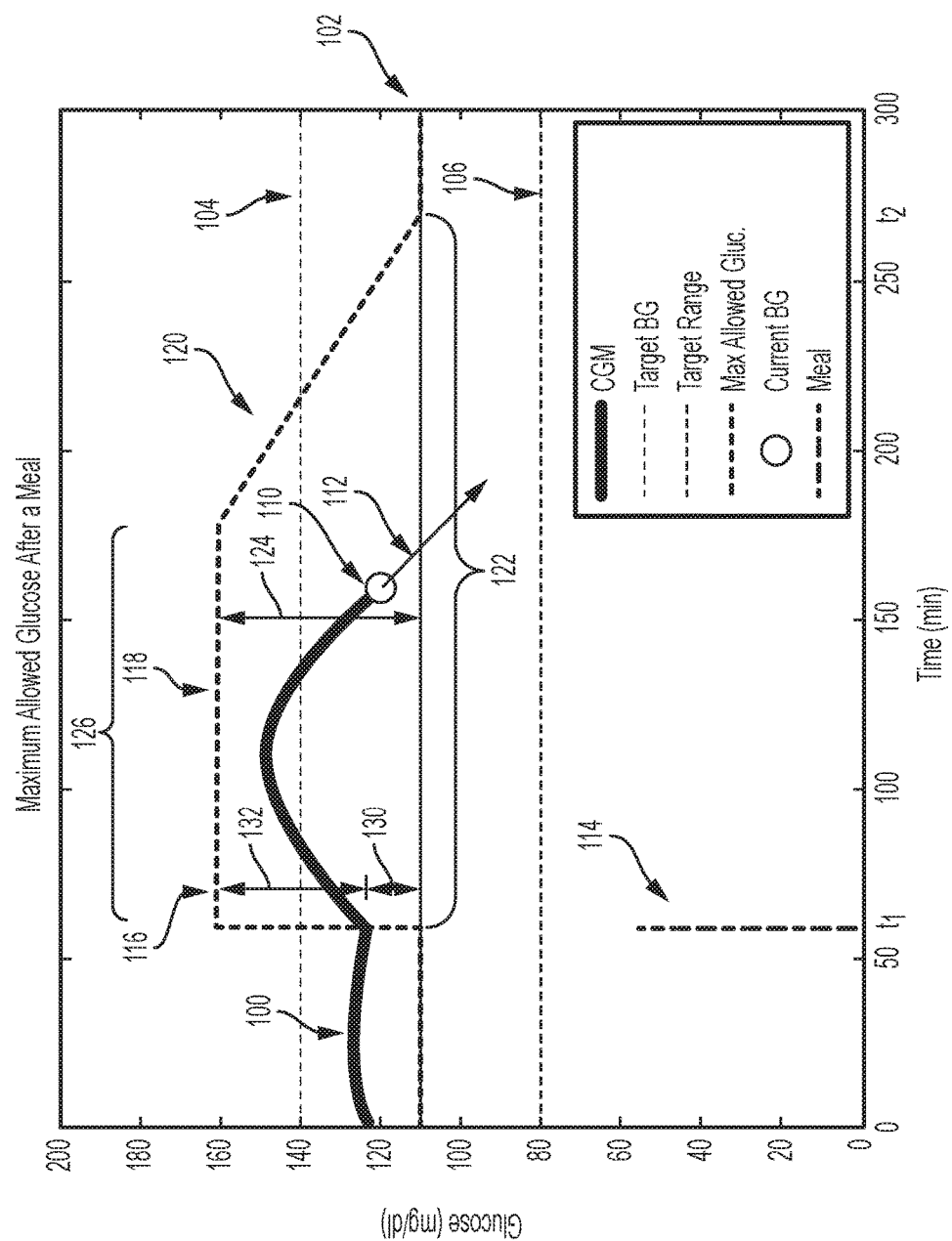
FIG. 3 illustrates a graph plotting an exemplary CGM trace and an adjusted maximum allowed glucose following a meal event.

Referring to FIG. 3, an exemplary CGM trace 100 is illustrated, wherein the x-axis represents time in minutes and the y-axis represents glucose in mg/dl. CGM trace 100 comprises a series of detected glucose levels measured over a period. In the illustrated embodiment, CGM trace 100 represents filtered glucose levels, i.e., glucose levels that are estimated based on the measured glucose levels weighted with the probably of sensor accuracy. A most recent estimated glucose level 110 has an associated negative rate of change indicated with arrow 112. Bolus calculator module 48 determines the target glucose level 102 and a target range of glucose levels indicated with an upper glucose limit 104 and a lower glucose limit 106. For illustrative purposes, target glucose level 102 is 110 mg/dl, upper glucose limit 104 is 140 mg/dl, and lower glucose limit 106 is 80 mg/dl, although other suitable values may be provided. Bolus calculator module 48 may determine target glucose level 102 and limits 104, 106 based at least in part on the user's history data described herein. Management device 26 uses the trending glucose data of CGM trace 100 to recommend corrective action to move the blood glucose towards the target glucose level 102. The target glucose level 102 of FIG. 3 corresponds to the maximum allowed glucose before time $t_1$ and after time $t_2$, i.e., when there has not been any recent meals or correction boluses. Between times $t_1$ and $t_2$, the maximum allowed glucose is adjusted based on a meal event 114 or other suitable events.

At time $t_1$, meal event 114 occurs when the user consumes a meal and enters carbohydrate data into management device 26 indicating the amount of carbohydrates consumed with the meal. In some instances, an insulin bolus is administered at about the time of the meal event 114 to offset the expected increase in glucose levels resulting from the meal. Bolus calculator module 48 determines a projected glucose level rise and a duration of the glucose rise based on the carbohydrates consumed, the insulin correction bolus (if administered), and the user's historical data related to glucose swings following meals and insulin injections. Based on the projected glucose rise, bolus calculator module 48 determines an allowed rise value 124, an offset time value 126, and an acting time value 122. The allowed rise value 124 may be based on other events, such as a glucagon injection, exercise, sleep, driving, or time of day, for example.

The allowed rise value 124 is the amount by which the glucose level of the user may be allowed to increase with respect to the target glucose level 102 as a result of the carbohydrate intake and insulin bolus. In some embodiments, the allowed rise value 124 is the combination of a correction delta glucose value 130 resulting from an insulin bolus and a meal rise value 132 resulting from the meal event 114. The correction delta glucose value 130 is the difference between the current glucose level and the target glucose level 102 at the time of the insulin bolus to allow time for the glucose level to decrease following insulin. As illustrated, the allowed rise value 124 is constant (see line 118) for a first predetermined amount of time after the meal and insulin administration, i.e., offset time 126, and then decreases linearly (see slope 120) following the offset time 126. The total time that the meal and insulin dose have an effect on the bG levels of a patient is the acting time 122. FIG. 3 illustrates a trapezoid-shaped graph 116 of the allowed rise value 124 accounting for the effect of a dose of insulin and meal event.

The maximum allowed glucose increases based on allowed rise value 124 and follows plot 116 of FIG. 3. As such, bolus calculator module 48 expands the range of allowable glucose levels after a meal event for the duration of the acting time 122 according to plot 116. The allowed rise value 124 illustratively has an initial height of 50 mg/dl, but could have other suitable heights based on the meal size, the insulin, and the user's typical reactions to boluses from the historical data. In some embodiments, for meal events above a threshold amount of carbohydrates, the meal rise value 132 is fixed. As one example, the offset time 126 is about two hours, and the acting time 122 is about three to five hours, depending on the user, the meal size, and the insulin bolus.

Referring again to FIG. 2, management device 26 further includes basal rate adjustment logic 50 operative to calculate and adjust a basal rate based on the current glucose state and the risk associated with the current glucose state. Management device 26 transmits an adjustment to the basal rate in a control signal to insulin pump 31 via communication link 35, and insulin pump 31 adjusts the current insulin basal rate based on the adjustment. Alternatively, the adjusted basal rate may be displayed to the user, and the user manually adjusts the basal rate of insulin pump 31. In one or more embodiment, the adjustment is a percent reduction to the initial, unadjusted or nominal basal rate based on a risk of hypoglycemia or a percent increase to the initial, unadjusted or nominal basal rate based on risk of hyperglycemic conditions.

The basal rate adjustment logic 50 determines whether the basal rate is to be adjusted. If an adjusted basal rate is proper, basal rate adjustment logic 50 calculates an adjusted basal rate and management device 26 transmits a control signal to insulin pump 31 to cause insulin pump 31 to deliver insulin at the adjusted basal rate. Alternatively, management device 26 may display the adjusted basal rate to the user to prompt the user for manual adjustment of the insulin pump 31. In some embodiments, the implementation of the adjusted basal rate may be overridden by the user via manual control of the insulin pump 31.

However, because control-to-range control of the continuous glucose monitoring system 10 must be able to work for a variety of people with diabetes and various lifestyles, the aggressiveness of the control-to-range control may be adjusted. Aggressiveness is the willingness of the CGM system 10 to increase the insulin delivered to the PWD 11. A more aggressive system is more likely to give more insulin to the PWD which results in more negative glucose velocities. The individual physiological characteristics and lifestyles of PWDs 11 may result in default settings for the control-to-range not being appropriate for every user of the continuous glucose monitoring system 10. Specifically, some PWD 11 may require a more hypoglycemic averse system or flexibility in their desired glucose range. Adjusting the aggressiveness of the control-to-range algorithm improves the safety of the continuous glucose monitoring system 10 by allowing the control-to-range to be customized to each PWD's 11 needs.

Additionally, the aggressiveness of the control-to-range may also be adjusted at different times of day or for different periods in the life cycle of the glucose sensor 16. For example, the aggressiveness may be reduced for the first day of use of a glucose sensor 16 and then subsequently increased when the glucose sensor 16 sensitivity has stabilized. The aggressiveness could also be reduced if no recent calibration blood glucose measurement has been taken. If no recent calibration blood glucose measurement has been taken, the accuracy of the CGM readings are less certain and the aggressiveness of the control-to-range is adjusted to account for the reduced confidence in the CGM reading accuracy.

As previously discussed, microcontroller 32 includes hazard analysis logic 40 that calculates target return paths from a plurality of initial glucose states to a target glucose state based on cumulative hazard values. FIGS. 5 and 6 illustrate an exemplary hazard function 80 for calculating a hazard value for a given glucose level ultimately utilized in determination of the cumulative hazard value. In one or more embodiments the hazard function 80 is defined by the following equation:

$$h(g)_{hyper} = \max(\alpha_{hyper} \cdot \alpha(\log(\max(g - \Delta g_{hyper} - \max(\Delta g_{hypo}, 0), 1))^c - \beta), 0) \quad (1)$$

$$h(g)_{hypo} = \min(\alpha(\log(\max(g - \Delta g_{hypo}, 1))^c - \beta), 0) \quad (2)$$

$$h(g) = \begin{cases} h_{MAX} & \text{if } g - \Delta g_{hyper} - \max(\Delta g_{hypo}, 0) \geq g_{MAX} \\ h_{MIN} & \text{if } g - \Delta g_{hypo} \leq g_{MIN} \\ h(g)_{hyper} & \text{if } h(g)_{hypo} \geq 0 \\ h(g)_{hypo} & \text{if } h(g)_{hypo} < 0 \end{cases} \quad (3)$$

where g is the blood glucose value (mg/dl) shown on the x-axis, h(g) is the corresponding hazard value shown on the y-axis, $\Delta g_{hyper}$ is a hyperglycemic shift, $\Delta g_{hypo}$ is a hypoglycemic shift, $h_{MAX}$ is a maximum hazard, $h_{MIN}$ is a minimum hazard, $\alpha_{hyper}$ is the hyperglycemic control aggressiveness, and $\alpha$, $\beta$, and c are process variables. Additional and alternate hazard functions are also envisioned as outlined in the numerous related applications incorporated by reference throughout this disclosure. In the illustrated embodiment, the variables $\alpha$, $\beta$, and c are defined as follows: $\alpha=1.509$, $\beta=5.381$, and $c=1.084$. $g_{MAX}$ is a glucose value above which no additional incremental hazard is calculated above $h_{MAX}$ and similarly $g_{MIN}$ is a glucose value below which no additional incremental hazard is calculated above $h_{MIN}$. Test cases of hazard functions for a hyperclycemic range ($h(g)_{hyper}$) and a hypoglycemic range ($h(g)_{hypo}$) are generated. The h(g) function determines if $h_{MAX}$, $h_{MIN}$, $h(g)_{hyper}$, or $h(g)_{hypo}$ should be implemented as the final hazard value for the tested blood glucose value.

Implementation of $g_{MAX}$ and $g_{MIN}$ in the determination of $h_{MAX}$ and $h_{MIN}$ respectively prevent excessively positive or negative hazard values for extreme blood glucose values. In one or more embodiments $g_{MAX}$ is set at 600 mg/dl and $h_{MAX}$ is the $h(g)_{hyper}$ associated with $g_{MAX}$. Similarly, in one or more embodiments $g_{MIN}$ is set at 10 mg/dl and $h_{MIN}$ is the $h(g)_{hypo}$ associated with $g_{MIN}$. As such, if g exceeds $g_{MAX}$ or drops below $g_{MIN}$, the hazard value associated with the blood glucose value is prevented from exceeding the range defined by $h_{MAX}$ and $h_{MIN}$.

In one or more embodiments, the aggressiveness of the control-to-range is adjusted with a scaling of the risk surface. Specifically, a hyperglycemia risk scaling method introduces a scaling factor into the hazard function that only applies toward positive hazard values associated with hyperglycemia. Implementation of this hyperglycemia risk scaling method is achieved with the parameter $\alpha_{hyper}$ which provides functionality to adjust the aggressiveness of the hyperglycemic hazard function ($h(g)_{hyper}$) to account for the varying insulin sensitivities of PwD. Instituting a scaling factor results in a gradual reduction of the aggressiveness of the hyperglycemia portion of the risk surface and a concomitant gradual reduction of the aggressiveness of the adjustments to the basal rate. In scaling only the hyperglycemia hazard function, the hypoglycemia hazard evaluation is not affected. However, in further embodiments, a scaling factor could also be applied to the hypoglycemia risk surface so that the hypoglycemia risk and the hyperglycemia risk can be scaled independently.

Figure 4A:
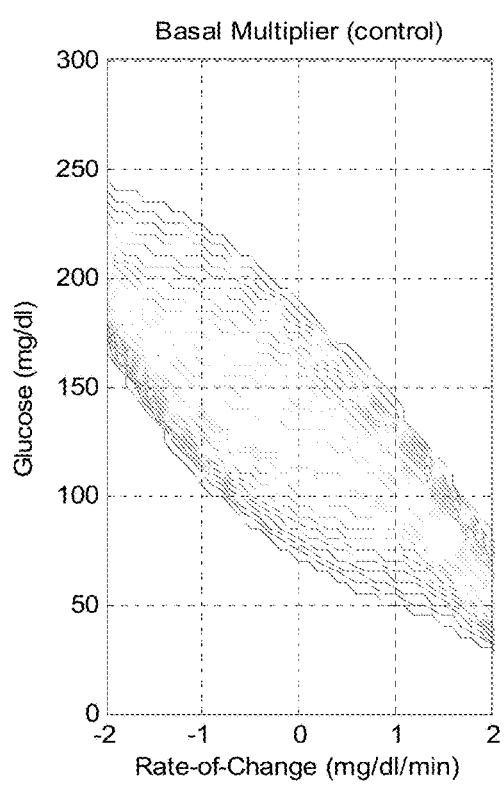
FIGS. 4A and 4B illustrate typical basal multipliers and basal multipliers with implementation of a risk scaling aggressiveness parameter respectively according to one or more embodiments shown and described herein.
Figure 4B:
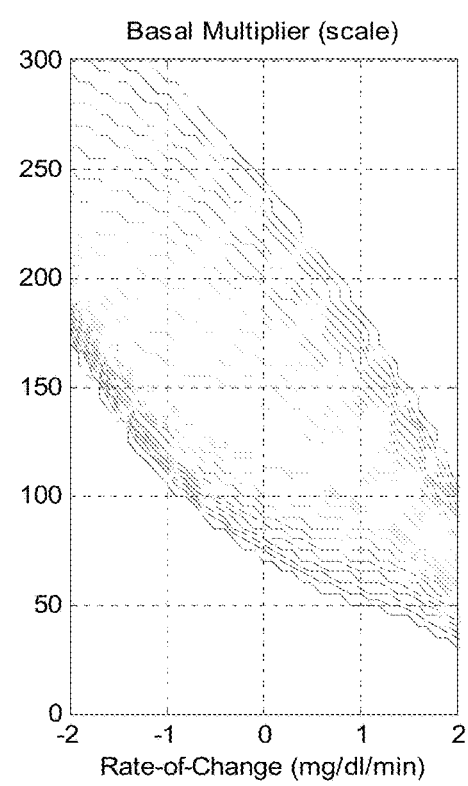

With reference to FIGS. 4A and 4B, typical basal multipliers and basal multipliers with risk scaling are provided respectively. With typical basal multiplier, as illustrated in FIG. 4A, the basal rate would be increased to 250% at about 190 mg/dl and 0 mg/dl/min. Conversely, with hyperglycemic risk scaling, as illustrated in FIG. 4B, the basal rate would be decreased to about 165% at about 190 mg/dl and 0 mg/dl/min. The decreased aggressiveness is evidenced in the reduction of the basal multiplier from 250% to 165% with the risk scaling. Additionally, with reference to FIG. 4C, a nominal hazard function 80 is shown along with a hazard function with reduced $\alpha_{hyper}$ 82 illustrating the gradual reduction of the aggressiveness of the hazard function in the hyperglycemic region.

In one or more embodiments, the aggressiveness of the control-to-range is adjusted with shifting of the risk surfaces. Specifically, a hyperglycemia risk shifting method shifts the hyperglycemic risk surface to account for insulin on board following a meal or correction bolus. The hyperglycemia risk shift may also be used when a larger glucose target range is recommended for a patient. For example, children typically use a larger glucose target range. In this case a minimum shift is used and any meal or bolus related shift is added. The hyperglycemic region of the risk surface is shifted by the meal rise or other shift in the maximum allowed glucose. In shifting only the hyperglycemia hazard function, the hypoglycemia hazard evaluation is not affected. Implementation of the hyperglycemic shift is illustrated in Equation 1 presented supra as the $\Delta g_{hyper}$ parameter.

Figure 4C:
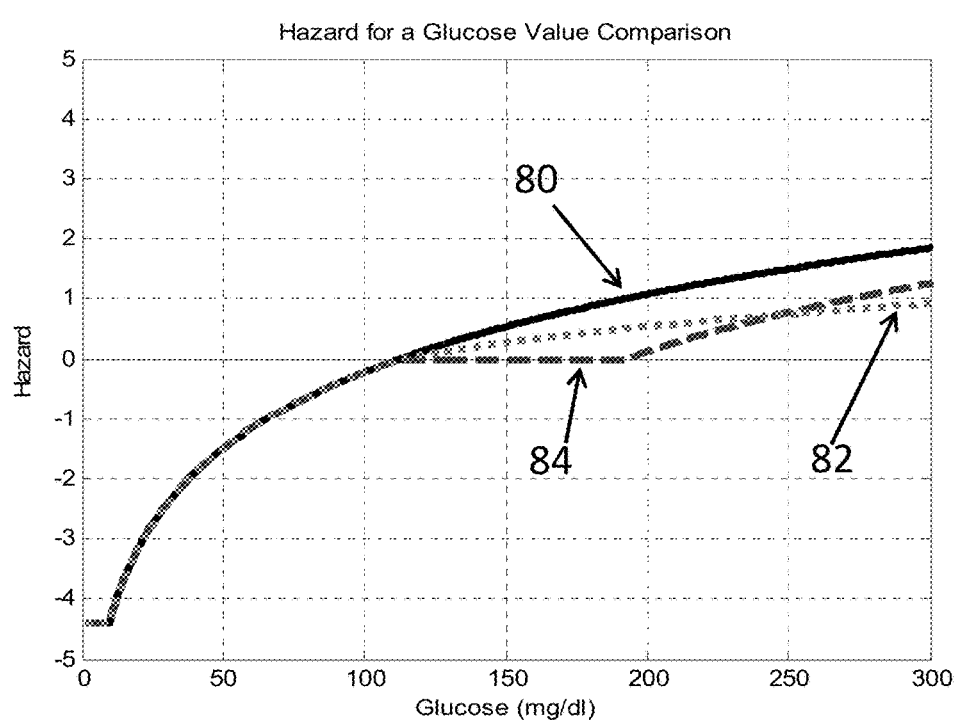
FIG. 4C illustrates a plot of a nominal hazard function and the hazard function with implementation of a hyperglycemic risk scaling and hyperglycemic risk shifting respectively.
Figure 5A:
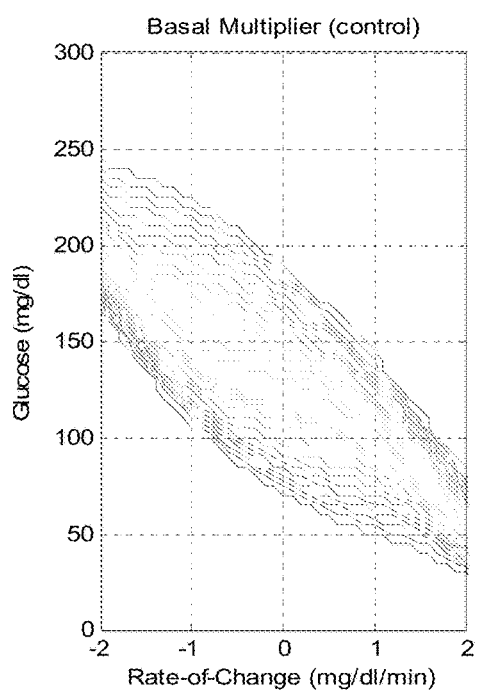
FIGS. 5A and 5B illustrate typical basal multipliers and basal multipliers with implementation of a risk shifting aggressiveness parameter respectively according to one or more embodiments shown and described herein.
Figure 5B:
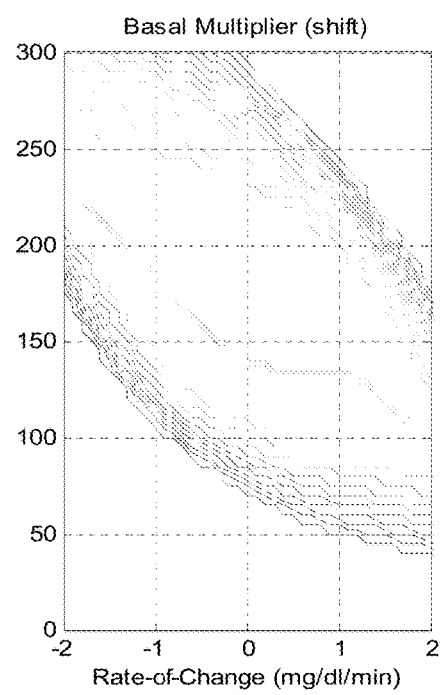

With reference to FIGS. 5A and 5B, typical basal multipliers and basal multipliers with risk shifting are provided respectively. With typical basal multipliers, as illustrated in FIG. 5A, the basal rate would be increased to 250% at about 190 mg/dl and 0 mg/dl/min. Conversely, with hyperglycemic risk shifting, as illustrated in FIG. 5B, the basal rate would remain substantially unchanged at about 100% at 190 mg/dl and 0 mg/dl/min. The decreased aggressiveness is evidenced in the reduction of the basal multiplier from 250% to 100% with the hypoglycemic risk shifting. With reference to FIG. 4C, $\Delta g_{hyper}$ shifts the hazard function 80 in the hyperglycemic region (positive hazard values) to account for a recent meal or correction bolus. Hyper shift hazard function 84 illustrates a shift in the hazard function after a previous meal or correction bolus.

In one or more embodiments, the aggressiveness of the control-to-range is adjusted with modification of the allowed glucose acceleration. Glucose acceleration is the rate of change of glucose velocity. Glucose velocity is the rate of change of glucose value. As such glucose acceleration may have units of mg/dl/min$^2$ and glucose velocity may have units of mg/dl/min.

The risk surface calculation uses a parameter for the maximum allowed glucose acceleration when determining the hazard associated with a specific glucose state. Specifically, the cumulative hazard value of a return path from the current glucose state to the target glucose utilizes the maximum allowed glucose acceleration. A default value of glucose acceleration is 0.025 mg/dl/min$^2$ and adjusting the glucose acceleration value affects the shape of the risk surface. The maximum positive glucose acceleration and the maximum negative glucose acceleration may be different absolute values. If a person has glucagon available then their maximum positive acceleration may be increased while their maximum negative acceleration may remain unchanged. The availability of glucagon allows an overly aggressive insulin bolus or basil rate to be corrected.

The cumulative hazard value of a return path from the current glucose state to the target glucose state is calculated by summing the hazard values of the glucose values on the path between the current glucose state and the target glucose state. The path is constrained by limiting the maximum allowed glucose acceleration. Additionally, the target is assumed to have a rate-of-change of zero as once the target glucose state is reached it is desired to remain at the target glucose state and not oscillate above and below the target glucose state.

The return path of minimum risk between the glucose state and the target is the fastest path. This return path uses the maximum allowed glucose accelerations, both positive and negative glucose accelerations, to return to the target glucose state. The closed form solution to the return path generation is composed of a time period with one extreme of the allowed glucose accelerations followed by the opposite extreme.

If a positive hypoglycemic shift is being used then the hypoglycemic shift must be added to the target glucose to get the shifted glucose target. This is necessary to correctly shift the hypoglycemic risk as the glucose target represents the blood glucose level where the hazard shifts from positive (hyperglycemic) to negative (hypoglycemic). The adjustment of the target glucose to the shifted glucose target is defined by the following equation:

$$\hat{g}_t = g_t + \max(\Delta g_{hypo}, 0) \quad (4)$$

where $\hat{g}_t$ is the shifted glucose target, $g_t$ is the nominal glucose target, and $\Delta g_{hypo}$ is the hypoglycemic shift. The maximum function in equation 4 prevents a negative hypoglycemic shift from being added to the target glucose and instead uses a hypoglycemic shift of zero resulting in $\hat{g}_t$ and $g_t$ being equal.

As an initial matter, the generalized form of the return path must be determined. The return path may have an initial positive glucose acceleration followed by a negative glucose acceleration or may have an initial negative glucose acceleration followed by a positive glucose acceleration. The generalized form of the return path may be determined by solving which of equation 5 and equation 6, presented infra, returns a real number solution.

$$T^{\pm} = t_1^{\pm} + t_2^{\pm} \quad (5)$$

$$T^{\mp} = t_1^{\mp} + t_2^{\mp} \quad (6)$$

where $$t_1^{\pm} = \frac{\sqrt{\ddot{g}_n(\ddot{g}_p - \ddot{g}_n)(-\dot{g}^2 + 2\ddot{g}_p - 2\hat{g}_t\ddot{g}_p)} - \dot{g}\ddot{g}_p + \dot{g}\ddot{g}_n}{\ddot{g}_p(\ddot{g}_p - \ddot{g}_n)}, \quad (7)$$

$$t_2^{\pm} = \frac{\dot{g} + \ddot{g}_p t_1^{\pm}}{-\ddot{g}_n}, \quad (8)$$

$$t_1^{\mp} = \frac{\sqrt{\ddot{g}_p(\ddot{g}_n - \ddot{g}_p)(-\dot{g}^2 + 2\ddot{g}_n - 2\hat{g}_t\ddot{g}_n)} - \dot{g}\ddot{g}_n + \dot{g}\ddot{g}_p}{\ddot{g}_n(\ddot{g}_n - \ddot{g}_p)}, \quad (9)$$

$$t_2^{\mp} = \frac{\dot{g} + \ddot{g}_n t_1^{\mp}}{-\ddot{g}_p}, \quad (10)$$

$\dot{g}$ is the rate of change of the glucose level, $\ddot{g}_p$ is the maximum positive glucose acceleration, $\ddot{g}_n$ is the maximum negative glucose acceleration, and $\hat{g}_t$ is the shifted glucose target from equation 4. If equation 5 returns a real number for $T^{\pm}$ and both $t_1^{\pm}$ and $t_2^{\pm}$ are greater than or equal to zero, the return path utilizes a positive acceleration first and a negative acceleration second. Conversely, if equation 6 returns a real number for $T^{\mp}$ and both $t_1^{\mp}$ and $t_2^{\mp}$ are greater than or equal to zero, the return path utilizes a negative acceleration first and a positive acceleration second.

Once the generalized form of the return path is determined, the cumulative hazard value of the return path may be calculated. When the return path utilizes a positive acceleration first, the cumulative hazard value is defined by the following equation:

$$h(g, \dot{g}) = \sum_{t=0}^{t_1^{\pm}} h\left(g + \dot{g}t + \frac{1}{2}\ddot{g}_p t^2\right) + \sum_{t=0}^{t_2^{\pm}} h\left(\hat{g}_t + \frac{1}{2}\ddot{g}_n t^2\right) \quad (11)$$

and when the return path utilizes a negative acceleration first, the cumulative hazard value is defined by the following equation:

$$h(g,\dot{g}) = \sum_{t=0}^{t_1^{\mp}} h\left(g + \dot{g}t + \frac{1}{2}\ddot{g}_n t^2\right) + \sum_{t=0}^{t_2^{\mp}} h\left(\hat{g}_t + \frac{1}{2}\ddot{g}_p t^2\right). \quad (12)$$

It should be appreciated that return paths that encounter more extreme glucose values will tend to have a higher cumulative hazard value as the hazard value for each time point is higher as illustrated in FIG. 4C. For example, a blood glucose value of 225 mg/dl would have a higher hazard value than a blood glucose value of 120 mg/dl at the same glucose rate-of-change. Also, paths that take a longer time to return to the target glucose state will tend to have a higher hazard value. A path may require longer returning to the target glucose state as a result of initial glucose rate-of-change or extreme glucose values.

In one or more embodiments, the allowed acceleration is increased. Increasing the allowed acceleration results in a reduced risk for larger rates of change in glucose concentration because the CGM system 10 assumes that it is easier to recover from an undesirable glucose state with the higher allowed maximum acceleration. Adjusting the control-to-range system with an increased maximum allowed acceleration causes the control-to-range system to wait longer to reduce the basal insulin rate when blood glucose is falling which thereby increases the aggressiveness. With reference to FIGS. 6A and 6B, the basal rate when the rate of change in the glucose concentration (glucose velocity) is zero are almost identical between the default settings and the control-to-range system with the increased aggressiveness from an increased maximum allowed acceleration implemented. The resulting negative slope of the basal multiplier with respect to the rate of change of the glucose concentration is reduced.

In one or more embodiments, the allowed acceleration is decreased. Decreasing the allowed acceleration results in the CGM system 10 calculating a greater risk for increased rates of change in the glucose concentration. The increased calculated risk in rate of change of the blood glucose concentration deviating from zero makes the CGM system 10 react quickly to any drop or rise in glucose. The CGM system 10 aggressively manages any deviation from a zero rate of change in glucose concentration. With reference to FIGS. 7A and 7B, the basal rate when the rate of change in the glucose concentration (glucose velocity) is zero are almost identical between the default settings and the control-to-range system with the increased aggressiveness from an increased maximum allowed acceleration implemented. The resulting negative slope of the basal multiplier with respect to the rate of change of the glucose concentration is increased.

In one or more embodiments, the risk is determined by summing the hazard of a range of glucose states multiplied by the probability of that state. The glucose state uncertainty controls the calculation of the probability of a given state. As previously discussed, the uncertainty is typically produced by the Kalman filter. If the uncertainty remains high for an extended period of time or crosses a specific threshold then the PWD 11 is notified and the control algorithm may be changed from control-to-range to predictive low glucose suspend (pLGS). If the uncertainty crosses a more extreme threshold, the control system may be turned off until the glucose sensor 16 of the CGM system 10 is recalibrated or replaced.

The cumulative hazard value provides the hazard for a specific return path from the current glucose state to the target glucose state. However, there are uncertainties in CGM blood glucose measurements from glucose sensor 16. As such, the true blood glucose measurement may vary from the blood glucose determined by the glucose sensor 16 and the specific calculated cumulative hazard value may be inaccurate with regards to the actual return path. To account for the variability in the true return path, a current risk metric is determined which accounts for variance in the CGM blood glucose measurements.

To calculate the current risk metric, a predicted glucose state at an intermediate point of the CTR period is initially determined. In various embodiments, the intermediate point of the CTR period is the true midpoint (½ of the CTR period), ¼ of the CTR period, ⅓ of the CTR period, ⅔ the CTR period, or ¾ of the CTR period. In an embodiment, the CTR is typically updated every 15 minutes resulting in the midpoint being 7.5 minutes into the 15 minute sampling interval. For short time horizons a linear prediction performs as well or better than more complicated models, so a linear prediction is used for simplicity. The rate-of-change in the glucose level is assumed to remain constant over the 7.5 min window in determining the predicted blood glucose level at the midpoint of the 15 minute sampling interval. As such, the predicted glucose level is defined by the following equation:

$$\hat{g} = g + \dot{g}\tau \quad (13)$$

where g is the initial measured blood glucose level, $\dot{g}$ is the initial rate-of-change of the glucose level, and $\tau$ is the prediction time measured from the beginning of the CTR period. The predicted glucose state is thus $[\hat{g}, \dot{g}]$.

Subsequently, a glucose state distribution around the predicted glucose state is determined. Similarly, a glucose state distribution around the current glucose state may also be determined. The samples for the glucose state distribution are selected based on the standard deviation of the distribution in the g and $\dot{g}$ directions. Generation of the glucose state distribution samples is defined by the following equations:

$$G_s = \left[g - 2\sigma_g, g - 2\sigma_g + \frac{4\sigma_g}{k}, g - 2\sigma_g + 2\frac{4\sigma_g}{k}, \right. \quad (14)$$
$$\left. g - 2\sigma_g + 3\frac{4\sigma_g}{k}, \ldots, g - 2\sigma_g + k\frac{4\sigma_g}{k}\right]$$

$$\dot{G}_s = \left[\dot{g} - 2\sigma_{\dot{g}}, \dot{g} - 2\sigma_{\dot{g}} + \frac{4\sigma_{\dot{g}}}{n}, \dot{g} - 2\sigma_{\dot{g}} + 2\frac{4\sigma_{\dot{g}}}{n}, \right. \quad (15)$$
$$\left. \dot{g} - 2\sigma_{\dot{g}} + 3\frac{4\sigma_{\dot{g}}}{n}, \ldots, \dot{g} - 2\sigma_{\dot{g}} + n\frac{4\sigma_{\dot{g}}}{n}\right]$$

where $G_s$ is the distribution of glucose values, $\dot{G}_s$ is the distribution of glucose rates of change, g is the glucose value for the current risk metric, $\dot{g}$ is the rate of change of the glucose level for the current risk metric, $\sigma_g$ is the standard deviation of g, $\sigma_{\dot{g}}$ is the standard deviation of $\dot{g}$, k is the number of divisions of $G_s$, and n is the number of divisions of $\dot{G}_s$. It will be appreciated that g may represented the current glucose level or the predicted glucose level if the glucose state distribution is desired for the current glucose state or the predicted glucose state respectively. Equation 14 and equation 15 provide a distribution of samples ranging within two standard deviations of g and $\dot{g}$. In at least one embodiment, the sampled values for g are selected by dividing the range bounded by two standard deviations by 10 and the sampled values for $\dot{g}$ are selected by dividing the range bounded by two standard deviations by 8 such that k=10 and n=8 respectively.

The current risk metric is determined based on a weighted average of the cumulative hazard values of the return paths generated from each of the sampled glucose states. Specifically, the risk is calculated by determining the weighted average of the cumulative hazard values at each combination of points in $G_s$ and $\dot{G}_s$ and weighting them by a multivariate exponential function $w(g_s, \dot{g}_s)$. The current risk metric is defined by the following equation:

$$r = \frac{\sum_{G_s} \sum_{\dot{G}_s} h(g_s, \dot{g}_s) w(g_s, \dot{g}_s)}{\sum_{G_s} \sum_{\dot{G}_s} w(g_s, \dot{g}_s)} \tag{16}$$

where r is the current risk metric, $$w(g_s, \dot{g}_s) = \exp\left(-\frac{1}{2}[g_s - g \quad \dot{g}_s - \dot{g}] P_g^{-1} \begin{bmatrix} g_s - g \\ \dot{g}_s - \dot{g} \end{bmatrix}\right), \tag{17}$$

$G_s$ is the distribution of glucose values and $\dot{G}_s$ is the distribution of glucose rates of change determined from the glucose state distribution around the detected glucose state, $h(g_s, \dot{g}_s)$ is the cumulative hazard value of the return path at each glucose state, g is the glucose value for the current risk metric, $\dot{g}$ is the rate of change of the glucose level for the current risk metric, $$P_g = \begin{bmatrix} \sigma_g^2 & \sigma_g \sigma_{\dot{g}} \\ \sigma_{\dot{g}} \sigma_g & \sigma_{\dot{g}}^2 \end{bmatrix}, \tag{18}$$

$\sigma_g$ is the standard deviation of g, and $\sigma_{\dot{g}}$ is the standard deviation of $\dot{g}$. The weighting of the cumulative hazard values results in samples closest to the measured glucose state receiving the largest weight in the final current risk metric calculation.

Figure 8A:
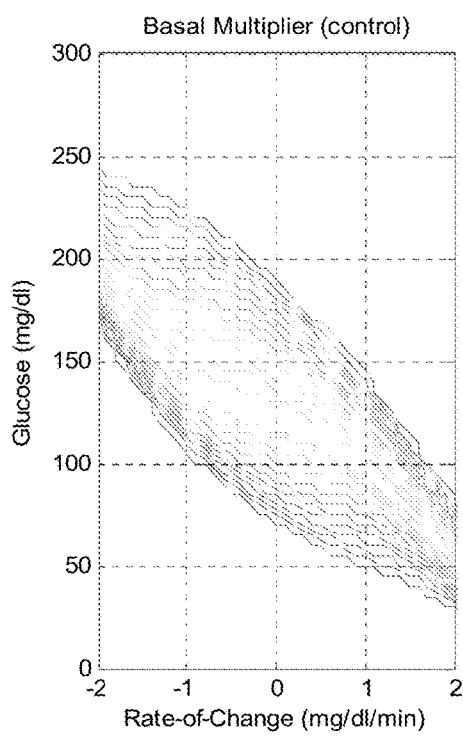
FIGS. 8A and 8B illustrate typical basal multipliers and basal multipliers with implementation of an increased uncertainty aggressiveness parameter respectively according to one or more embodiments shown and described herein.
Figure 8B:
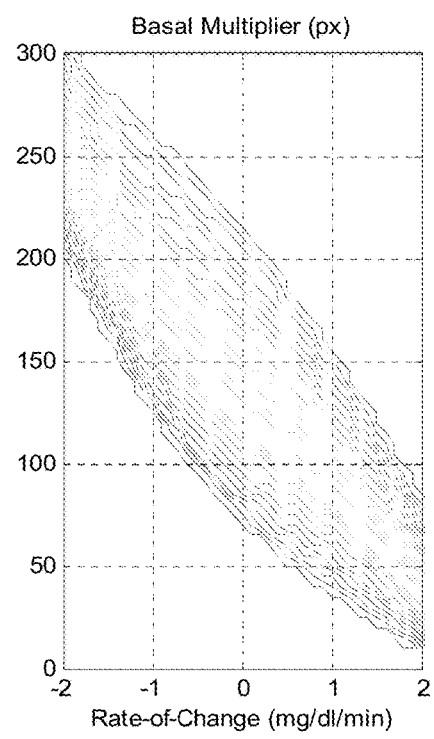

In one or more embodiments, the uncertainty in the glucose state is increased. Increasing the uncertainty causes an increase in the probability of hypoglycemia. Additionally, since the hazard function is asymmetric, the increased probability of hypoglycemia leads to an increase in the risk of hypoglycemia. The increase in the risk of hypoglycemia results in the control-to-range system reacting sooner to increases in rates of change of blood glucose (glucose velocity) and also decreases the aggressiveness of a basal increase in the hyperglycemic region. With reference to FIGS. 8A and 8B, the basal multiplier of a typical uncertainty and an increased uncertainty are provided respectively. With a typical uncertainty, as illustrated in FIG. 8A, the basal rate would be increased to 250% at about 190 mg/dl and 0 mg/dl/min. Conversely, with an increased uncertainty, as illustrated in FIG. 8B, the basal rate would be increased to about 210% at about 190 mg/dl and 0 mg/dl/min. The decreased aggressiveness is evidenced in the reduction of the basal multiplier from 250% to 210% with an increase in the uncertainty of the glucose state.

Figure 9A:
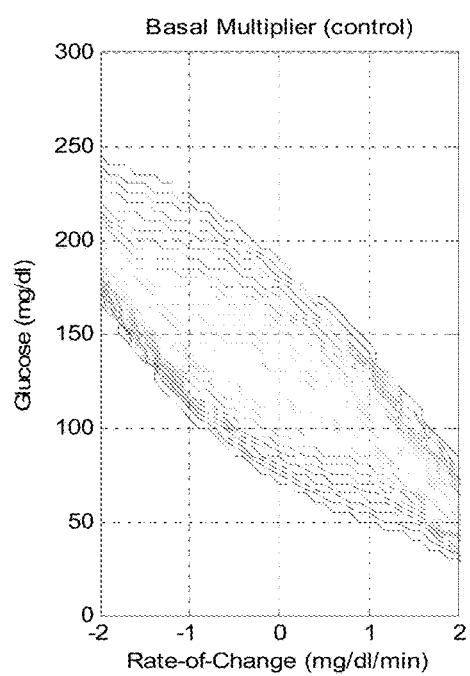
FIGS. 9A and 9B illustrate typical basal multipliers and basal multipliers with implementation of a decreased uncertainty aggressiveness parameter respectively according to one or more embodiments shown and described herein.
Figure 9B:
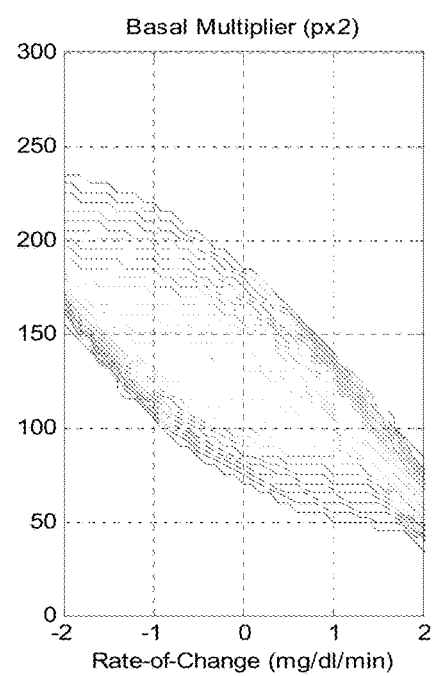

In further embodiments, the uncertainty in the glucose state is decreased. Decreasing the uncertainty causes the control-to-range system to increase its trust in the glucose state. The increase in the trust in the glucose state results in the control-to-range system reacting more slowly to increases in rates of change of blood glucose (glucose velocity) and also increases the aggressiveness of a basal increase in the hyperglycemic region. The control-to-range system may react more slowly to increases in rates of change of blood glucose because the probability of actually being in hypoglycemia is reduced with the decreased uncertainty in the glucose state. With reference to FIGS. 9A and 9B, the basal multiplier of a typical uncertainty and a decreased uncertainty are provided respectively. The region where no adjustment to the basal rate is requested is increased with a decreased uncertainty in the glucose state as shown in a comparison of FIGS. 9A and 9B.

Each of the aggressiveness parameters may be adjusted by the PWD 11 manually or by the control-to-range algorithm based on other factors such as exercise, stress, sleep, travel, age, and/or illness.

The glucose uncertainty and/or acceleration parameters may be used in an algorithm to determine the risk surface and/or basal multiplier profile, but not exposed to the PWD 11 or user. For example, the PWD 11 or user may be given the choice of low, medium, or high aggressiveness which adjusts maximum allowed glucose acceleration, hyperglycemic risk shifting, hypoglycemic risk shifting, and risk scaling to achieve the desired result. The abstract setting of low, medium, or high aggressiveness may be achieved without alerting the PWD 11 or HCP to the particular values utilized for the 4 aggressiveness parameters. It will be appreciated that additional levels of aggressiveness may also be implemented such as medium-low and medium-high or a scale of 1-10 representing 10 distinct aggressiveness strata.

In further embodiments, the HCP and PWD 11 may define a specific range which is set using the hyperglycemic shift parameter and an aggressiveness which is set using the scaling factor and acceleration.

The parameters which determine aggressiveness of the CGM system 10 may be set when the CGM system 10 is first prescribed and then optimized over time. In some embodiments the aggressiveness setting could be medium as the default setting with adjustment to a more aggressive high setting or a less aggressive low setting.

In adjusting and/or determining the aggressiveness setting, the HCP and/or PWD 11 may look to the sensitivity of the PWD 11 to both negative and positive glucose velocities. Some people are distressed as much by a rapid negative glucose velocity when their blood glucose is still at a good range as they are by going hypoglycemic. Additionally, the HCP could utilize a questionnaire to gauge the PWD's 11 fear of hypoglycemia, the PWD's 11 degree of knowledge regarding times of hypoglycemia, and the number of recent severe hypoglycemic episodes as a guide for selecting the aggressiveness setting of low, medium, or high.

The final basal multiplier for each CTR period is determined utilizing the current risk metric. The current risk metric is first converted to a basal multiplier value between 0 and $TBR_{MAX}$. $TBR_{MAX}$ is the maximum percentage for a temporary basal rate (TBR). In at least one embodiment, the $TBR_{MAX}$ defaults to 250%. In further embodiments, the $TBR_{MAX}$ is lower or higher than 250% and is adjusted to tune the control and determination for hypo-adverse individuals. The basal multiplier value is defined by the following equation:

$$BM(r) = \begin{cases} \dfrac{r - r_{0\%}}{-r_{0\%}}, & r > r_{0\%} \\ 0, & r \leq r_{0\%} \end{cases} \tag{19}$$

where BM(r) is the basal multiplier value, r is the current risk metric, and $r_{0\%}$ is a reference risk metric. In one or more embodiments, the reference risk metric is a glucose state linked to complete basal shutoff. For example, complete basal shutoff may occur at 70 mg/dl such that when the blood glucose level is below 70 mg/dl no basal insulin is provided. The basal multiplier value may be provided as a continuous function as the current risk metric varies. However, before providing the adjusted basal rate to the therapy delivery device 31 it is converted to the nearest TBR increment ($TBR_{inc}$) to provide an incremental basal rate multiplier ($BM_{inc}$). The incremental basal rate multiplier is defined by the following equation:

$$BM_{inc} = \min\left(\max\left(\text{floor}\left(\frac{BM(r)}{TBR_{inc}}\right)TBR_{inc}, 0\right), TBR_{MAX}\right). \quad (20)$$

With reference to FIG. 9, exemplary continuous basal multiplier values and incremental basal rate multipliers with a $TBR_{inc}$ of 10% and the implemented floor function are illustrated.

It is to be appreciated that a barrier to adoption of an automatic control strategy for insulin delivery systems has been the uncertainty in the input data, i.e. the glucose values, from a continuous glucose sensor(s). Great effort has been made in improving the accuracy and reliability. For example, even with impedance data being used to adjust the data from the glucose sensor to improve the accuracy of the reported value, a reliability of 100% is probably not likely to be achieved. For this reason, a gain control module may evaluate the quality of the sensor data, and accounts for the quality in the control algorithm. Specifically, the inventors have discovered that a probability score derived from the time course of sensor data and used to adapt the gain of a statistical filter can improve the quality of the reported value. The Sensor Quality Score $Q_{total}$ can also be used to adapt the controller gain of the insulin delivery system, such that the aggressiveness of the control can be traded off against the safety of the user based on the degree of confidence in the sensor glucose results.

The aggressiveness of the controller can be adjusted using the Sensor Quality Score. In the case of proportional-integral-derivative controller (PID) control, the controller is specified with three gain terms.

$$u(t) = K_p e(t) + K_i \int_0^t e(\tau)d\tau + K_d \frac{de(t)}{dt} \quad (21)$$

The Sensor Quality Score may be used to adjust some set of the gain terms.

$$K_p = Q_{total} k_p \quad (22)$$

$$K_i = Q_{total} k_i \quad (23)$$

$$K_d = Q_{total} k_d \quad (24)$$

Additionally the Sensor Quality Score can be used when calculating the integral term so that past errors that occur when the sensor quality is low have less impact on the current controller output.

$$u(t) = K_p e(t) + K_i \int_0^t Q_{total}(\tau)e(\tau)d\tau + K_d \frac{de(t)}{dt} \quad (25)$$

The aggressiveness of the controller may also be adjusted using a hyper shift, hyper scaling, max allowed glucose acceleration, or glucose state uncertainty. The hyper shift may be zero when $Q_{total}$ is one and increase as it decreases toward zero. The hyper scaling may be equal to $Q_{total}$ or a factor of it. The glucose state uncertainty is adjusted by incorporating the $Q_{total}$ value into the recursive filter.

The quality of data being evaluated is assessed in terms of a total quality score $Q_{total}$ from a set of quality metrics, e.g., of signal input characteristic(s) and data received from the glucose sensor 16 and/or an impedance sensor. The total quality score $Q_{total}$ has a value that ranges from zero (0) to (one) 1, and is used to alter the gain of the microcontroller 32 to provide an increased level of safety when the quality score is low, and to improve microcontroller performance and glycemic control when the quality score is high.

For example, in one illustrated implementation, in the case of a sensor 16 with a total quality score, $Q_{total}=0$ (or $0 \le Q_{total} < T$), the microcontroller 32 if operating in closed-loop glucose control, in which insulin delivery adjustments are made automatically by the microcontroller 32 based on the received input from the glucose sensor 16, would fall back to a safer, open-loop mode of operation, i.e., open-loop glucose control, in which adjustments are made by the user and as recommended to the user by pre-programmed time profiles. In the case of the total quality score $Q_{total}$ being greater than a threshold value T and/or equal to one (1), i.e., $T < Q_{total} \le 1$, the microcontroller 32 acts more aggressively to manage glycemia with the certainty that the sensor data will enable the system to deliver the proper amount of insulin, thereby allowing, e.g., the system 10 to function in optimal closed-loop glucose control with optimal safety.

In another implementation, in the case of the total quality score $Q_{total}$ being greater than a threshold value $T_{high}$ and/or equal to one (1), i.e., $T_{high} < Q_{total} \le 1$, the microcontroller 32 acts aggressively to manage glycemia with the certainty that the sensor data will enable the system to deliver the proper amount of insulin, thereby allowing, e.g., the system 10 to function in optimal closed-loop glucose control with optimal safety. In the case of a glucose sensor 16 with a total quality score, $Q_{total}$ such that $T_{low} \le Q_{total} < T_{high}$, where $T_{low} < T_{high}$ the microcontroller 32 would fall back to a safer, reduced-gain closed-loop mode of operation, in which adjustments are made automatically by the microcontroller, but with a reduced gain based on the value of the total quality score through implementation of equations 21-25. In the case of a sensor 16 with a total quality score, $Q_{total}$ such that $0 \le Q_{total} < T_{low}$, the microcontroller would fall back to a safer, open-loop mode of operation, i.e., open-loop glucose control, in which adjustments are made by the user and as recommended to the user by pre-programmed time profiles and as recommended to the user by pre-programmed time profiles For further and alternative descriptions for probability based controller gain and $Q_{total}$, see U.S. patent application Ser. No. 15/061,202, filed on Mar. 4, 2016, entitled "Probability Based Controller Gain," the entire disclosure of which is incorporated by reference herein. For further and alternative descriptions for determining the basal rate adjustment, see U.S. patent application Ser. No. 14/229,016, filed on Mar. 28, 2015, entitled "System and Method for Adjusting Therapy Based on Risk Associated with a Glucose State," the entire disclosure of which is incorporated by reference herein. For further description of calculating the target return paths and calculating risk metrics, see U.S. patent application Ser. No. 13/645,198, filed on Oct. 4, 2012, entitled "System and Method for Assessing Risk Associated with a Glucose State," the entire disclosure of which is incorporated by reference herein. For further description of the probability analysis tool, the recursive filter, the uncertainty calculation, and other probability and risk analysis functionalities of computing device 66, see U.S. patent application Ser. No. 12/693,701, filed on Jan. 26, 2010, entitled "Methods and Systems for Processing Glucose Data Measured from a Person Having Diabetes," and U.S. patent application Ser. No. 12/818,795, filed on Jun. 18, 2010, entitled "Insulin Optimization Systems and Testing Methods with Adjusted Exit Criterion Accounting for System Noise Associated with Biomarkers," the entire disclosures of which are incorporated by reference herein. For further description of the bolus calculator module 88, see U.S. patent application Ser. No. 13/593,557, filed on Aug. 24, 2012, entitled "Handheld Diabetes Management Device with Bolus Calculator," and U.S. patent application Ser. No. 13/593,575, filed on Aug. 24, 2012, entitled "Insulin Pump and Methods for Operating the Insulin Pump," the entire disclosures of which are incorporated by reference herein.

It should now be understood that the methods and systems described herein may be used to estimate the glucose level of a person having diabetes and utilize a control-to-range algorithm to adjust the glucose level of a person having diabetes. Furthermore, the methods and systems described herein may also be used to tune the aggressiveness of the control-to-range algorithm to reliably increase insulin basal rates to account for increases in glucose concentration. The methods described herein may be stored on a computer-readable medium which has computer-executable instructions for performing the methods. Such computer-readable media may include compact discs, hard drives, thumb drives, random-access memory, dynamic random-access memory, flash memory, and so forth.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A method of determining a basal rate adjustment of insulin in a continuous glucose monitoring system of a person with diabetes, the method comprising:
receiving, by at least one computing device, a signal representative of at least one glucose measurement;
detecting, by the at least one computing device, a glucose state of the person based on the signal, the detected glucose state including a glucose level of the person and a rate of change of the glucose level;
determining, by the at least one computing device, a current risk metric, the current risk metric indicating a risk of at least one of a hypoglycemic condition and a hyperglycemic condition of the person, wherein determining the current risk metric comprises determining, by the at least one computing device, a return path based on a transition from the detected glucose state to a target glucose state, the return path comprising at least one intermediate glucose value associated with a return to the target glucose state;
determining, by the at least one computing device, a cumulative hazard value of the return path, the cumulative hazard value including a sum of the hazard values of the at least one glucose value on the return path, each hazard value being indicative of a hazard associated with the corresponding intermediate glucose value; and
determining, by the at least one computing device, a weighted average of cumulative hazard values of return paths generated from a glucose state distribution around the detected glucose state; and
calculating, by the at least one computing device, an adjustment to a basal rate of a therapy delivery device based on the current risk metric and a control-to-range algorithm comprising at least one aggressiveness parameter, the aggressiveness parameter selected from:
(a) scaling of a risk surface generated based on the risk metric with a scaling factor to adjust positive hazard values associated with hyperglycemia;
(b) shifting of a risk surface generated based on the risk metric to account for insulin on board following a meal or correction bolus;
(c) adjustment to a maximum allowed glucose acceleration, glucose acceleration representing the rate of change of glucose velocity and glucose velocity representing the rate of change of glucose values;
(d) adjustment to a glucose state uncertainty representing the level of trust in the measured glucose state; or
(e) combinations thereof.

2. The method of claim 1, further comprising displaying to a user, on a graphical user interface, graphical data representative of the calculated adjustment to the basal rate.

3. The method of claim 1, further comprising transmitting a control signal to instruct the therapy delivery device to adjust the basal rate based on the calculated adjustment.

4. The method of claim 3, wherein the therapy delivery device includes an insulin pump for delivering insulin to the person with diabetes, and the therapy delivery device is in communication with the at least one computing device for receiving the calculated adjustment of the basal rate.

5. The method of claim 1, wherein the hazard value for each of the hazard values of the at least one glucose value on the return path is determined by the at least one computing device in accordance with $$h(g)_{hyper} = \max(\alpha_{hyper} \cdot \alpha(\log(\max(g - \Delta g_{hyper} - \max(\Delta g_{hypo}, 0), 1))^c - \beta), 0),$$

$$h(g)_{hypo} = \min(\alpha(\log(\max(g - \Delta g_{hypo}, 1))^c - \beta), 0), \text{ and}$$

$$h(g) = \begin{cases} h_{MAX} & \text{if } g - \Delta g_{hyper} - \max(\Delta g_{hypo}, 0) \geq g_{MAX} \\ h_{MIN} & \text{if } g - \Delta g_{hypo} \leq g_{MIN} \\ h(g)_{hyper} & \text{if } h(g)_{hypo} \geq 0 \\ h(g)_{hypo} & \text{if } h(g)_{hypo} < 0 \end{cases}$$

where g is the glucose value, $\Delta g_{hyper}$ is a hyperglycemic shift to account for a recent meal or correction bolus, $\Delta g_{hypo}$ is a hypoglycemic shift to account for recent exercise or glucagon, $h_{MAX}$ is a maximum hazard value representing the hazard for a glucose value of 600 mg/dl, $g_{MAX}$ is a glucose value above which no additional imcremental hazard is calculated above $h_{MAX}$, $h_{MIN}$ is a minimum hazard representing the hazard value for a glucose value of 10 mg/dl, $g_{MIN}$ is a glucose value below which no additional incremental hazard is calculated above $h_{MIN}$, $\alpha_{hyper}$ is the hyperglycemic control aggressiveness to adjust for insulin sensitivity, and $\alpha$, $\beta$, and c are process variables.

6. The method of claim 1, further comprising generating a basal multiplier plot based on the current risk metric.

7. The method of claim 1, wherein
if $T^{\pm}=t_1^{\pm}+t_2^{\pm}$ is a real number, the cumulative hazard value of the return path is determined by the at least one computing device according to $$h(g,\dot{g}) = \sum_{t=0}^{t_1^{\pm}} h\left(g + \dot{g}t + \frac{1}{2}\ddot{g}_p t^2\right) + \sum_{t=0}^{t_2^{\pm}} h\left(\dot{g}_t + \frac{1}{2}\ddot{g}_n t^2\right)$$

where $$t_1^{\pm} = \frac{\sqrt{\ddot{g}_n(\ddot{g}_p - \ddot{g}_n)(-\dot{g}^2 + 2\ddot{g}_p - 2\dot{g}_t\ddot{g}_p)} - \dot{g}\ddot{g}_p + \dot{g}\ddot{g}_n}{\ddot{g}_p(\ddot{g}_p - \ddot{g}_n)}, t_2^{\pm} = \frac{\dot{g} + \ddot{g}_p t_1^{\pm}}{-\ddot{g}_n}, \dot{g}$$

is the rate of change of the glucose level, $\ddot{g}_p$ is the maximum positive glucose acceleration, and $\ddot{g}_n$ is the maximum negative glucose acceleration or
if $T^{\mp}=t_1^{\mp}+t_2^{\mp}$ is a real number, the cumulative hazard value of the return path is determined by the at least one computing device according to $$h(g,\dot{g}) = \sum_{t=0}^{t_1^{\mp}} h\left(g + \dot{g}t + \frac{1}{2}\ddot{g}_n t^2\right) + \sum_{t=0}^{t_2^{\mp}} h\left(\dot{g}_t + \frac{1}{2}\ddot{g}_p t^2\right)$$

where $$t_1^{\mp} = \frac{\sqrt{\ddot{g}_p(\ddot{g}_n - \ddot{g}_p)(-\dot{g}^2 + 2\ddot{g}_n - 2\dot{g}_t\ddot{g}_n)} - \dot{g}\ddot{g}_n + \dot{g}\ddot{g}_p}{\ddot{g}_n(\ddot{g}_n - \ddot{g}_p)}, t_2^{\mp} = \frac{\dot{g} + \ddot{g}_n t_1^{\mp}}{-\ddot{g}_p}, \dot{g}$$

is the rate of change of the glucose level, $\ddot{g}_p$ is the maximum positive glucose acceleration, and $\ddot{g}_n$ is the maximum negative glucose acceleration.

8. The method of claim 1, wherein only the risk surface representing hyperglycemic risk is shifted.

9. The method of claim 8, wherein the shift in the hyperglycemic risk surface corrects for insulin on board following a meal or correction bolus.

10. The method of claim 1, wherein the maximum allowed glucose acceleration is increased.

11. The method of claim 1, wherein the maximum allowed glucose acceleration is decreased.

12. The method of claim 1, wherein the glucose state uncertainty is produced by a Kalman filter.

13. The method of claim 1, wherein the glucose state distribution is determined by the at least one computing device according to $$G_s = \left[g - 2\sigma_g, g - 2\sigma_g + \frac{4\sigma_g}{k}, g - 2\sigma_g + 2\frac{4\sigma_g}{k},\right.$$
$$\left. g - 2\sigma_g + 3\frac{4\sigma_g}{k}, \ldots, g - 2\sigma_g + k\frac{4\sigma_g}{k}\right] \text{ and}$$

$$\dot{G}_s = \left[\dot{g} - 2\sigma_{\dot{g}}, \dot{g} - 2\sigma_{\dot{g}} + \frac{4\sigma_{\dot{g}}}{n}, \dot{g} - 2\sigma_{\dot{g}} + 2\frac{4\sigma_{\dot{g}}}{n},\right.$$
$$\left.\dot{g} - 2\sigma_{\dot{g}} + 3\frac{4\sigma_{\dot{g}}}{n}, \ldots, \dot{g} - 2\sigma_{\dot{g}} + n\frac{4\sigma_{\dot{g}}}{n}\right]$$

where $G_s$ is the distribution of glucose values, $\dot{G}_s$ is the distribution of glucose rates of change, g is the glucose value for the current risk metric, $\dot{g}$ is the rate of change of the glucose level for the current risk metric, $\sigma_g$ is the standard deviation of g, $\sigma_{\dot{g}}$ is the standard deviation of $\dot{g}$, k is the number of divisions of $G_s$, and n is the number of divisions of $\dot{G}_s$.

14. The method of claim 1, wherein the current risk metric is determined by the at least one computing device according to $$r = \frac{\sum_{G_s}\sum_{\dot{G}_s} h(g_s, \dot{g}_s) w(g_s, \dot{g}_s)}{\sum_{G_s}\sum_{\dot{G}_s} w(g_s, \dot{g}_s)}$$

where r is the current risk metric, $$w(g_s, \dot{g}_s) = \exp\left(-\frac{1}{2}[g_s - g \quad \dot{g}_s - \dot{g}]P_g^{-1}\begin{bmatrix}g_s - g\\ \dot{g}_s - \dot{g}\end{bmatrix}\right),$$

$G_s$ is the distribution of glucose values and $\dot{G}_s$ is the distribution of glucose rates of change determined from the glucose state distribution around the detected glucose state, $h(g_s, \dot{g}_s)$ is the cumulative hazard value of the return path at each glucose state, g is the glucose value for the current risk metric, $\dot{g}$ is the rate of change of the glucose level for the current risk metric, $$P_g = \begin{bmatrix}\sigma_g^2 & \sigma_g\sigma_{\dot{g}}\\ \sigma_{\dot{g}}\sigma_g & \sigma_{\dot{g}}^2\end{bmatrix},$$

$\sigma_g$ is the standard deviation of g, and $\sigma_{\dot{g}}$ is the standard deviation of $\dot{g}$.

15. A blood glucose management device configured to determine a basal rate adjustment in a continuous glucose monitoring system of a person with diabetes, the device comprising:
a non-transitory computer-readable medium storing executable instructions; and
at least one processing device configured to execute the executable instructions such that, when executed by the at least one processing device, the executable instructions cause the at least one processing device to:
receive a signal representative of at least one glucose measurement;
detect a glucose state of the person based on the signal, the detected glucose state including a glucose level of the person and a rate of change of the glucose level;

determine a current risk metric, the current risk metric indicating a risk of at least one of a hypoglycemic condition and a hyperglycemic condition of a person, wherein determining the current risk metric comprises determining, by the at least one computing device, a return path based on a transition from the detected glucose state to a target glucose state, the return path comprising at least one intermediate glucose value associated with a return to the target glucose state;

determining, by the at least one computing device, a cumulative hazard value of the return path, the cumulative hazard value including a sum of the hazard values of the at least one glucose value on the return path, each hazard value being indicative of a hazard associated with the corresponding intermediate glucose value; and determining, by the at least one computing device, a weighted average of cumulative hazard values of return paths generated from a glucose state distribution around the detected glucose state; and calculate an adjustment to a basal rate of a therapy delivery based on the current risk metric and a control-to-range algorithm comprising at least one aggressiveness parameter, the aggressiveness parameter selected from:

(a) scaling of a risk surface generated based on the risk metric with a scaling factor to adjust positive hazard values associated with hyperglycemia;

(b) shifting of a risk surface generated based on the risk metric to account for insulin on board following a meal or correction bolus;

(c) adjustment to a maximum allowed glucose acceleration, glucose acceleration representing the rate of change of glucose velocity and glucose velocity representing the rate of change of glucose values;

(d) adjustment to a glucose state uncertainty representing the level of trust in the measured glucose state; or (e) combinations thereof.

* * * * *

UNITED STATES PATENT AND TRADEMARK OFFICE
CERTIFICATE OF CORRECTION

| | |
|---|---|
| PATENT NO. | : 10,332,633 B2 |
| APPLICATION NO. | : 15/170450 |
| DATED | : June 25, 2019 |
| INVENTOR(S) | : David L. Duke et al. |

It is certified that error appears in the above-identified patent and that said Letters Patent is hereby corrected as shown below:

In the Claims

In Column 21, Line 1, delete "imcremental" and insert --incremental--, therefor.

Signed and Sealed this
Eighteenth Day of February, 2020

Andrei Iancu
*Director of the United States Patent and Trademark Office*